United States Patent
Friedman et al.

(10) Patent No.: US 7,358,274 B2
(45) Date of Patent: Apr. 15, 2008

(54) METHODS FOR TREATING OR PREVENTING CANCER USING BENZOPYRANONE COMPOUNDS

(75) Inventors: Glenn Friedman, Encinitas, CA (US); Jeffrey McKie, San Diego, CA (US); Jonathan Wright, San Diego, CA (US); Sophie Perrin-Ninkovic, Carlsbad, CA (US); Bernd M. Stein, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 11/431,056

(22) Filed: May 9, 2006

(65) Prior Publication Data

US 2006/0194866 A1 Aug. 31, 2006

Related U.S. Application Data

(62) Division of application No. 10/685,722, filed on Oct. 14, 2003, now Pat. No. 7,091,235.

(60) Provisional application No. 60/418,469, filed on Oct. 15, 2002.

(51) Int. Cl.
  A61K 31/4025 (2006.01)
  C07D 405/12 (2006.01)
(52) U.S. Cl. ............. 514/422; 548/400; 548/517; 514/428
(58) Field of Classification Search ........ 548/400, 548/517; 514/422, 428
  See application file for complete search history.

(56) References Cited

U.S. PATENT DOCUMENTS

| | | |
|---|---|---|
| 6,291,456 B1 | 9/2001 | Stein et al. |
| 6,331,562 B1 | 12/2001 | Bhagwat et al. |
| 6,372,739 B1 | 4/2002 | Stein et al. |
| 6,620,838 B1 | 9/2003 | McKie et al. |
| 2003/0149025 A1 | 8/2003 | Zeldis |

FOREIGN PATENT DOCUMENTS

| | | |
|---|---|---|
| WO | WO 00/39120 | 7/2000 |
| WO | WO 01/49673 | 7/2001 |

OTHER PUBLICATIONS

Al-Saffar et al., 1996, "Assessment of the role of GM-CSF in the cellular transformation and the development of erosive lesions around orthopaedic implants", Am J Clin Pathol. 105(5):628-39.
Alonzi et al., 1998, "Interleukin 6 is required for the development of collagen-induced arthritis", J Exp Med. 187(4):461-8.
Barkhem et al., 1998, "Differential response of estrogen receptor alpha and estrogen receptor beta to partial estrogen agonists/antagonists", Mol Pharmacol. 54(1):105-12.
Bismar et al., 1995, "Increased cytokine secretion by human bone marrow cells after menopause or discontinuation of estrogen replacement", J Clin Endocrinol Metab. 80(11):3351-5.
Bodine et al., 1998, "Estrogen receptor-alpha is developmentally regulated during osteoblast differentiation and contributes to selective responsiveness of gene expression", Endocrinology. 139(4):2048-57.
Brandenberger et al., 1998, "Estrogen receptor alpha (ER-alpha) and beta (ER-beta) mRNAs in normal ovary, ovarian serous cystadenocarcinoma and ovarian cancer cell lines: down-regulation of ER-beta in neoplastic tissues", J Clin Endocrinol Metab. 83(3):1025-8.
Chen et al., 2001, "Molecular basis for the constitutive activity of estrogen-related receptor alpha-I", J Biol Chem. 276(30):28465-70.
Chung et al., 2002, "Resistance to tamoxifen-induced apoptosis is associated with direct interaction between Her2/neu and cell membrane estrogen receptor in breast cancer", Int J Cancer. 97(3):306-12.
Clinton and Hua, 1997, "Estrogen action in human ovarian cancer", Crit Rev Oncol Hematol. 25(1):1-9.
Cooke et al., 1998, "Mechanism of estrogen action: lessons from the estrogen receptor-alpha knockout mouse", Biol Reprod. 59(3):470-5.
Couse et al., 1997, "Tissue distribution and quantitative analysis of estrogen receptor-alpha (ERalpha) and estrogen receptor-beta (ERbeta) messenger ribonucleic acid in the wild-type and ERalpha-knockout mouse", Endocrinology. 138(11):4613-21.
Coward et al., 2001, "4-Hydroxytamoxifen binds to and deactivates the estrogen-related receptor gamma", Proc Natl Acad Sci U S A. 98(15):8880-4.

(Continued)

Primary Examiner—Golam M. M. Shameem
(74) Attorney, Agent, or Firm—Jones Day

(57) ABSTRACT

This invention relates to Benzopyranone Compounds, compositions comprising a Benzopyranone Compound and methods for treating or preventing cancer or inhibiting the growth of a cancer cell or neoplastic cell comprising administering an effective amount of a Benzopyranone Compound. The Benzopyranone Compounds have the formula:

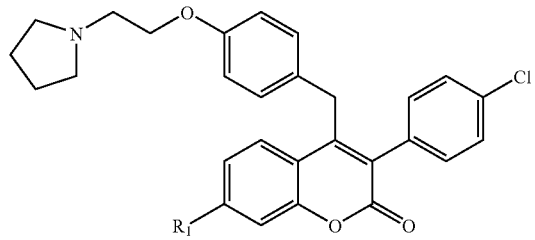

or a pharmaceutically acceptable salt thereof, wherein $R_1$ is halogen, trifluoromethyl or $C_{1-6}$ alkyl.

11 Claims, No Drawings

OTHER PUBLICATIONS

Das et al., 1997, "Estrogenic responses in estrogen receptor-α deficient mice reveal a distinct estrogen signaling pathway", Proc. Natl. Acad. Sci. USA 94:12786-91.

Devlin et al., 1998, "IL-6 mediates the effects of IL-1 or TNF, but not PTHrP or 1,25(OH)2D3, on osteoclast-like cell formation in normal human bone marrow cultures", J Bone Miner Res. Mar. 1998;13(3):393-9.

Duan et al., 1998, "Estrogen-induced c-fos protooncogene expression in MCF-7 human breast cancer cells: role of estrogen receptor Sp1 complex formation", Endocrinology. 139(4):1981-90.

Enmark et al., 1997, "Human estrogen receptor beta-gene structure, chromosomal localization, and expression pattern", J Clin Endocrinol Metab. 82(12):4258-65.

Eustace et al., 1993, "Interleukin-6 (IL-6) functions as an autocrine growth factor in cervical carcinomas in vitro", Gynecol Oncol. 50(1):15-19.

Farhat et al., 1996, "The vascular protective effects of estrogen", FASEB J. 10(5):615-24.

Garrett et al., 1997, "A murine model of human myeloma bone disease", Bone 20(6):515-20.

Girasole et al., 1992, "17 beta-estradiol inhibits interleukin-6 production by bone marrow-derived stromal cells and osteoblasts in vitro: a potential mechanism for the antiosteoporotic effect of estrogens", J Clin Invest. 89(3):883-91.

Grese et al., 1997, "Structure-activity relationships of selective estrogen receptor modulators: modifications to the 2-arylbenzothiophene core of raloxifene", J Med Chem. 40(2):146-67.

Gupta et al., 1985, "7-hydroxy-4-phenyl-3(4-hydroxyphenyl)-coumarin—a new interceptive agent", Indian J Exp Biol. 23(11):638-40.

Gustafsson et al., 1998, "Therapeutic potential of selective estrogen receptor modulators", Curr Opin Chem Biol. 2(4):508-11.

Hata et al., 1998, "Role of estrogen and estrogen-related growth factor in the mechanism of hormone dependency of endometrial carcinoma cells", Oncology. 55 Suppl 1:35-44.

Hughes et al., 1996, "Estrogen promotes apoptosis of murine osteoclasts mediated by TGF-beta", Nat Med. 2(10):1132-6.

Iafrati et al., 1997, "Estrogen inhibits the vascular injury response in estrogen receptor alpha-deficient mice", Nat Med. 3(5):545-8.

Jansson et al., 1994, "Estrogen induces a potent suppression of experimental autoimmune encephalomyelitis and collagen-induced arthritis in mice", J Neuroimmunol. 53(2):203-7.

Jeltsch et al., 1987, "Structure of the human oestrogen-responsive gene pS2", Nucleic Acids Res. 15(4):1401-14.

Jilka et al., 1995, "Estrogen loss upregulates hematopoiesis in the mouse: a mediating role of IL-6", Exp Hematol. 23(6):500-6.

Jilka et al., 1992, "Increased osteoclast development after estrogen loss: mediation by interleukin-6", Science 57(5066):88-91.

Kelly et al., 1999, "Estrogen Modulation of G-protein-coupled Receptors", Trends Endocrinol Metab. 10(9):369-374.

Kimble et al., 1996, "Estrogen deficiency increases the ability of stromal cells to support murine osteoclastogenesis via an interleukin-1 and tumor necrosisfactor-mediatedstimulation of macrophage colony-stimulating factor production", J Biol Chem. 271(46):28890-7.

Kimble et al., 1995, "Simultaneous block of interleukin-1 and tumor necrosis factor is required to completely prevent bone loss in the early postovariectomy period", Endocrinology. 136(7):3054-61.

Klein et al., 1991, "Murine anti-interleukin-6 monoclonal antibody therapy for a patient with plasma cell leukemia", Blood. 78(5):1198-204.

Klein et al., 1989, "Paracrine rather than autocrine regulation of myeloma-cell growth and differentiation by Interleukin-6", Blood. 73(2):517-26.

Koo et al., 1992, "Interleukin-6 and renal cell cancer: production, regulation, and growth effects", Cancer Immunol Immunother. 35(2):97-105.

Korach et al., 1994, "Insights from the study of animals lacking functional estrogen receptor", Science 266(5190):1524-7.

Krege et al., 1998, "Generation and reproductive phenotypes of mice lacking estrogen receptor beta", Proc Natl Acad Sci U S A.95(26):15677-82.

Kuiper et al., 1997, "Comparison of the ligand binding specificity and transcript tissue distribution of estrogen receptors alpha and beta", Endocrinology. Mar. 1997;138(3):863-70.

Kurihara et al., 1989, "Generation of osteoclasts from isolated hematopoietic progenitor cells", Blood 74(4):1295-302.

Laflamme et al., 1998, "Expression and neuropeptidergic characterization of estrogen receptors (ERalpha and ERbeta) throughout the rat brain: anatomical evidence of distinct roles of each subtype", J Neurobiol. 36(3):357-78.

Lednicer et al., 1965, "Mammalian Antifertility Agents: Basic Ethers of 3,4—Diphenylcoumarin", J. Med. Chem. 8:725-726.

Leisten, 1990 Interleukin-6 serum levels correlate with footpad swelling in adjuvant-induced arthritic Lewis rats treated with cyclosporin A or indomethacin. Clin Immunol Immunopathol. Jul;56(1):108-15.

Levin et al., 1999, "Cellular Functions of the Plasma Membrane Estrogen Receptor", Trends Endocrinol Metab. 10(9):374-377.

Lorenzo et al., 1987, "Colony-stimulating factors regulate the development of multinucleated osteoclasts from recently replicated cells in vitro", J Clin Invest. 80(1):160-4.

Lu et al., 2001, "Transcriptional regulation of the estrogen-inducible pS2 breast cancer marker gene by the ERR family of orphan nuclear receptors", Cancer Res. 15;61(18):6755-61.

MacDonald et al., 1986, "Effects of human recombinant CSF-GM and highly purified CSF-1 on the formation of multinucleated cells with osteoclast characteristics in long-term bone marrow cultures", J Bone Miner Res. 1(2):227-33.

Martinez-Maza et al., 1992, "IL6 and AIDS", Res Immunol. 143(7):764-9.

Micheli et al., 1962, "Coumestrol, Plant Phenolics, and Synthetic Estrogens: a Correlation of Structure and Activity", 321-335.

Nadal et al., 2001, "The plasma membrane estrogen receptor: nuclear or unclear?", Trends Pharmacol Sci. 22(12):597-9.

Ogawa et al., 1997, "Behavioral effects of estrogen receptor gene disruption in male mice", Proc Natl Acad Sci U S A.94(4):1476-81.

Ohshima et al., 1998, "Interleukin 6 plays a key role in the development of antigen-induced arthritis", Proc Natl Acad Sci U S A.95(14):8222-6.

Okamoto et al., 1997, "Interleukin-6 as a paracrine and autocrine growth factor in human prostatic carcinoma cells in vitro", Cancer Res. 57(1):141-6.

Okamoto et al., 1997, "Autocrine effect of androgen on proliferation of an androgen responsive prostatic carcinoma cell line, LNCAP: role of interleukin-6", Endocrinology. 138(11):5071-4.

Pacifici 1996, "Estrogen, cytokines, and pathogenesis of postmenopausal osteoporosis", J Bone Miner Res. 11(8):1043-51.

Paech et al., 1997, "Differential ligand activation of estrogen receptors ERalpha and ERbeta at AP1 sites", Science. 277(5331):1508-10.

Parfitt et al., 1996, "A new model for the regulation of bone resorption, with particular reference to the effects of bisphosphonates", J Bone Miner Res. 11(2):150-9.

Passeri et al., 1993, "Increased interleukin-6 production by murine bone marrow and bone cells after estrogen withdrawal", Endocrinology. 133(2):822-8.

Poli et al., 1994, "Interleukin-6 deficient mice are protected from bone loss caused by estrogen depletion", EMBO J. 13(5):1189-96.

Pollard et al., 1968, "The oestrogenic and anti-oestrogenic activity of some synthetic steroids and non-steroids", Steroids.

Ray et al., 1987, "Enhanced antifertility activity of non-steroidal molecules with 3-n-butylamino-2-hydroxypropyloxy side chain", Contraception.35(3):283-7.

Reddy et al., 1994, "Interleukin-6 antisense deoxyoligonucleotides inhibit bone resorption by giant cells from human giant cell tumors of bone", J Bone Miner Res. 9(5):753-7.

Rissman et al., 1997, "Estrogen receptors are essential for female sexual receptivity", Endocrinology 138(1):507-10.

Rissman et al., 1997, "Estrogen receptor function as revealed by knockout studies: neuroendocrine and behavioralaspects", Horm Behav. 31(3):232-43.

Rohlff et al., 1998, "Prostate cancer cell growth inhibition by tamoxifen is associated with inhibition of protein kinase C and induction of p21 (waf1/cip1)", Prostate. 37(1):51-9.

Sar et al., 1999, "Differential expression of estrogen receptor-beta and estrogen receptor-alpha in the rat ovary", Endocrinology. 140(2):963-71.

Schiller et al., 1997, "17Beta-estradiol antagonizes effects of 1alpha,25-dihydroxyvitamin D3 on interleukin-6 production and osteoclast-like cell formation in mouse bone marrow primary cultures", Endocrinology 138(11):4567-71.

Shinar et al., 1990, "The effect of hemopoietic growth factors on the generation of osteoclast-like cells in mouse bone marrow cultures", Endocrinology 126(3):1728-35.

Shughrue et al., 1997, "Responses in the brain of estrogen receptor alpha-disrupted mice", Proc Natl Acad Sci USA.94(20):11008-12.

Shughrue et al., 1997, "The distribution of estrogen receptor-beta mRNA in forebrain regions of the estrogen receptor-alpha knockout mouse", Endocrinology. 138(12):5649-52.

Shughrue et al., 1997, "Comparative distribution of estrogen receptor-alpha and -beta mRNA in the rat central nervous system", J Comp Neurol. 388(4):507-25.

Siegall et al., 1990, "Expression of the interleukin 6 receptor and interleukin 6 in prostate carcinoma cells", Cancer Res. 50(24):7786-8.

Simpson et al., 1998, "Estrogen regulation of transforming growth factor-alpha in ovarian cancer", J Steroid Biochem Mol Biol. 64(3-4):137-45.

Stein et al., 1995, "Repression of the interleukin-6 promoter by estrogen receptor is mediated by NF-kappa B and C/EBP beta", Mol Cell Biol. 15(9):4971-9.

Suzuki et al., 1996, "Calcitonin-induced changes in the cytoskeleton are mediated by a signal pathway associated with protein kinase A in osteoclasts", Endocrinology. 137(11):4685-90.

Tartour et al., 1994, "Analysis of interleukin 6 gene expression in cervical neoplasia using a quantitative polymerase chain reaction assay: evidence for enhanced interleukin 6 gene expression in invasive carcinoma", Cancer Res. 54(23):6243-8.

Tremblay et al., 2001, 4-Hydroxytamoxifen is an isoform-specific inhibitor of orphan estrogen-receptor-related (ERR) nuclear receptors beta and gamma. Endocrinology 142(10):4572-5.

Tremblay et al., 1998, "EM-800, a novel antiestrogen, acts as a pure antagonist of the transcriptional functions of estrogen receptors alpha and beta", Endocrinology 139(1):111-8.

Tsukamoto et al., 1992, "Interleukin-6 in renal cell carcinoma", J. Urol. 148(6):1778-81; discussion 1781-2.

Turner et al., 1998, "Differential responses of estrogen target tissues in rats including bone to clomiphene, enclomiphene, and zuclomiphene", Endocrinology. 139(9):3712-20.

Verma et al., 1993, "Microwave induced alteration in the neuron specific enolase gene expression", Indian J. Chem. 32B:239-243.

Weissglas et al., 1997, "The role of interleukin-6 in the induction of hypercalcemia in renal cell carcinoma transplanted into nude mice", Endocrinology 138(5):1879-85.

Wendling et al., 1993, "Treatment of severe rheumatoid arthritis by anti-interleukin 6 monoclonal antibody", J. Rheumatol. 20(2):259-62.

Wyckoff et al., 2001, "Plasma membrane estrogen receptors are coupled to endothelial nitric-oxide synthase through Galpha(i)", J Biol Chem. 276(29):27071-6.

Yamashita et al., 1998, "Endocrine therapy in pancreatic carcinoma", Oncology. 55 Suppl 1:17-22.

Zhang et al., 1989, "Interleukin-6 is a potent myeloma-cell growth factor in patients with aggressive multiple myeloma", Blood. 74(1):11-3.

Cohen et al., 1976, "Acute Nonlymphocytic Leukemia Associated with Nitrosourea Chemotherapy: Report of Two Cases", Cancer Treat Rep. 60:1257-61.

Couldwell et al., 1996, "Treatment of Recurrent Malignant Gliomoas with Chronic Oral High Dose Tamoxifen", Clin. Cancer Res. 2:619-622.

Neubauer et al., 1995, "Raloxifene (LY156758) Produces Antimetastatic Responses and Extends Survival in the PAIII Rat Prostatic Adenocarcinoma Model", Prostate 27:220-9.

METHODS FOR TREATING OR PREVENTING CANCER USING BENZOPYRANONE COMPOUNDS

This application is a division of U.S. application Ser. No. 10/685,722, filed Oct. 14, 2003, now U.S. Pat. No. 7,091,235 currently allowed, which claims the benefit of U.S. provisional application No. 60/418,469, filed Oct. 15, 2002, the contents of which are incorporated by reference herein in their entirety.

1. FIELD OF THE INVENTION

This invention relates to Benzopyranone Compounds, compositions comprising a Benzopyranone Compound, and methods for using a Benzopyranone Compound to treat or prevent cancer.

2. BACKGROUND OF THE INVENTION

2.1 Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multi-step process that begins with minor pre-neoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

Descriptions of only a few types of cancers are provided below.

Characteristics of other types of cancers are well known to medical practitioners, and are described in the medical literature.

2.2 Brain Cancer and Brain Metastasis

There are about 10,000 incidences of brain tumors each year, and about 4000 incidences of spinal cord tumors each year (Komblith et al. (1985), *Cancer: Principles and Practice of Oncology*, $2^{nd}$ Ed., DeVita, V., Hellman, S., Rosenberg, S., eds., J. B. Lippincott Company, Philadelphia, Chapter 41: Neoplasms of the Central Nervous System). Central nervous system (CNS) tumors comprise the most common group of solid tumors in young patients (Id). Gliomas comprise about 60% of all primary CNS tumors, with the most common cerebral primary tumors being astrocytomas, meningioma, oligodendroglioma and histocytic lymphoma (Id). Gliomas usually occur in the cerebral hemispheres of the brain, but may be found in other areas such as the optic nerve, brain stem or cerebellum (Brain Tumor Society; www/tbts.org/primary.htm).

Gliomas are classified into groups according to the type of glial cell from which they originate (Id). The most common types of glioma are astrocytomas. These tumors develop from star-shaped glial cells called astrocytes. Astrocytomas are assigned to grades according to their malignancy. Low-grade astrocytomas, also known as grade I and II astrocytomas, are the least malignant, grow relatively slow and can often be completely removed using surgery. Mid-grade astrocytomas, also known as grade III astrocytomas, grow more rapidly and are more malignant. Grade III astrocytomas are treated with surgery followed by radiation and some chemotherapy. High-grade astrocytomas, also known as grade IV astrocytomas, grow rapidly, invade nearby tissue, and are very malignant. Grade IV astrocytomas are usually treated with surgery followed by a combination of radiation therapy and chemotherapy. Glioblastoma multiforme are grade IV astrocytomas, which are among the most malignant and deadly primary brain tumors (Id).

Traditionally, treatment of astrocytomas has involved surgery to remove the tumor, followed by radiation therapy. Chemotherapy may also be administered either before or after radiation therapy (Komblith et al. (1985), *Cancer: Principles and Practice of Oncology*, $2^{nd}$ Ed., DeVita, V., Hellman, S., Rosenberg, S., eds., J. B. Lippincott Company, Philadelphia, Chapter 41: Neoplasms of the Central Nervous System). While the same surgical techniques and principles have applied to treating glioblastoma multiforme and less malignant brain tumors, total removal of a glioblastoma multiforme tumor has been more difficult to achieve (Id).

The prognosis for a patient diagnosed as having a grade IV astrocytoma brain tumor has traditionally been poor. While a person treated for a grade I astrocytoma can commonly survive 10 years or more without recurrence, the mean length of survival for a patient with a grade IV astrocytoma tumor is 15 weeks after surgical treatment. Because of the high malignant-growth potential of grade IV astrocytoma tumors, only 5% of patients have survived for 1 year following surgical treatment alone, with a near 0% survival rate after 2 years. Radiation treatment in combination with surgical treatment increases the survival rate to about 10% after 2 years of treatment; however, virtually no patients survive longer than 5 years (Id).

2.3 Current Cancer Therapy

Currently, cancer therapy involves surgery, chemotherapy and/or radiation treatment to eradicate neoplastic cells in a patient (see, for example, Stockdale, 1998, "Principles of Cancer Patient Management", in *Scientific American: Medicine*, vol. 3, Rubenstein and Federman, eds., Chapter 12, Section IV). All of these approaches pose significant drawbacks for the patient. Surgery, for example, may be contraindicated due to the health of the patient or may be unacceptable to the patient. Additionally, surgery may not completely remove the neoplastic tissue. Radiation therapy is effective only when the irradiated neoplastic tissue exhibits a higher sensitivity to radiation than normal tissue, and radiation therapy can also often elicit serious side effects. (Id.) With respect to chemotherapy, there are a variety of chemotherapeutic agents available for treatment of neoplastic disease. However, despite the availability of a variety of chemotherapeutic agents, chemotherapy has many drawbacks (see, for example, Stockdale, 1998, "Principles Of Cancer Patient Management" in *Scientific American Medicine*, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, many tumor cells are resistant or develop resistance to chemotherapeutic agents through multi-drug resistance.

Nitrosourea chemotherapeutic agents have normally been used in the treatment of brain tumors. The key property of these compounds is their ability to cross the blood-brain barrier. 1-3-bis-2-chloroethyl-1-nitrosourea (BCNU, also known as Carmustine) was the first of these to be used clinically. While the use of BCNU in combination with surgery and/or radiation treatment has been shown to be beneficial, it has not cured glioblastoma multiforme brain tumors. Additionally, complications with prolonged nitrosourea treatment have been reported (Cohen et al., *Cancer Treat. Rep.* 60, 1257-1261 (1976)). These complications include pulmonary fibrosis, hepatic toxicity, renal failure and cases of secondary tumors associated with nitrosourea treatment.

The use of estrogen receptor modulators Tamoxifen and Raloxifene in cancer treatment has also been investigated. Tamoxifen has been used in human clinical trials involving the treatment of recurrent malignant glial tumors (Couldwell et al., *Clin. Cancer Res.* 2, 619-622 (1996)). Raloxifene has been shown to inhibit metastasis of a tail tumor to the lungs in a rat model (Neubauer et al., *Prostate* 27, 220-229 (1995)).

While a treatment regimen of surgery, radiation therapy and chemotherapy offers the opportunity for a modestly increased lifespan for patients with a grade IV astrocytoma brain tumor, the risks associated with each method of treatment are many. The benefits of treatment are minimal, and treatment can significantly decrease the quality of the patient's brief remaining lifespan.

Accordingly, there remains a clear need in the art for anti-cancer compounds and treatment methods that overcome the disadvantages of the above-mentioned traditional approaches.

Citation or identification of any reference in Section 2 of this application is not an admission that the reference is prior art to the present application.

3. SUMMARY OF THE INVENTION

The present invention relates to compounds of formula (I):

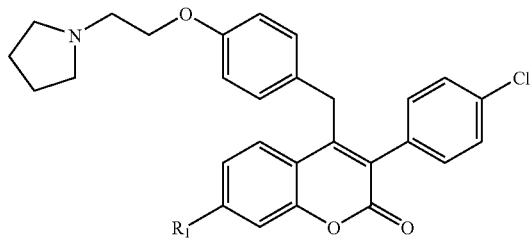

and pharmaceutically acceptable salt thereof, wherein $R_1$ is halogen, trifluoromethyl or $C_{1-6}$ alkyl.

A compound of formula (I) or a pharmaceutically acceptable salt thereof (each being a "Benzopyranone Compound") is useful for treating or preventing cancer in a patient.

The invention also relates to compositions comprising an effective amount of a Benzopyranone Compound and a pharmaceutically acceptable carrier or vehicle. The compositions are useful for treating or preventing cancer in a patient.

The invention further relates to methods for treating or preventing cancer, comprising administering to a patient in need thereof an effective amount of a Benzopyranone Compound.

The invention still further relates to methods for inhibiting the growth of a cancer cell or neoplastic cell, comprising contacting the cell with an effective amount of a Benzopyranone Compound.

4. DETAILED DESCRIPTION OF THE INVENTION

4.1 Definitions

As used herein, the term "$C_{1-6}$ alkyl" means a straight or branched non-cyclic hydrocarbon chain having from 1 to 6 carbon atoms. Representative straight chain $C_{1-6}$ alkyls include -methyl, -ethyl, -n-propyl, -n-butyl, -n-pentyl and -n-hexyl. Representative branched chain $C_{1-6}$ alkyls include -isopropyl, -sec-butyl, -isobutyl, -tert-butyl, -isopentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethtylbutyl, 1,2-dimethylbutyl, 1,3-dimethylbutyl, 2,2-dimethylbutyl, 2,3-dimethylbutyl and 3,3-dimethylbutyl.

As used herein, the term "$C_{1-4}$ alkyl" means a straight or branched non-cyclic hydrocarbon chain having from 1 to 4 carbon atoms. Representative straight chain $C_{1-4}$ alkyls include -methyl, -ethyl, -n-propyl and -n-butyl. Representative branched chain $C_{1-4}$ alkyls include -isopropyl, -sec-butyl, -isobutyl and -tert-butyl.

As used herein, the term "halogen" means fluoro, chloro, bromo or iodo.

As used herein, the terms "prevent", "preventing" and "prevention" include the prevention of the recurrence, spread or onset of cancer in a patient.

As used herein, the terms "treat", "treating" and "treatment" include the eradication, removal, modification, or control of primary, regional, or metastatic cancer tissue and the minimization or delay of the spread of cancer.

As used herein, the term "patient" means an animal, including, but not limited, to an animal such as a human, monkey, cow, horse, sheep, pig, chicken, turkey, quail, cat, dog, mouse, rat, rabbit or guinea pig, in one embodiment a mammal and in another embodiment a human. In certain embodiments, the patient can be an infant, adolescent or adult.

As used herein, the term "effective amount" when used in connection with a Benzopyranone Compound means an amount of the Benzopyranone Compound effective for treating or preventing cancer.

The phrase "pharmaceutically acceptable salt," as used herein includes, but is not limited to, salts of acidic or basic groups of a compound of formula (I). Compounds included in the present methods and compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present methods and compositions that include an amino moiety may form pharmaceutically or cosmetically acceptable salts with various amino acids, in addition to the acids mentioned above. Compounds, included in the present methods and compositions, that are acidic in nature are capable of forming base salts with various pharmacologically or cosmetically acceptable cations. Examples of such salts include alkali metal or alkaline earth metal salts and, particularly, calcium, magnesium, sodium lithium, zinc, potassium, and iron salts.

As used herein, the abbreviation "DMAP" means 4-dimethylaminopyridine.

As used herein, the abbreviation "DMF" means dimethylformamide.

As used herein, the abbreviation "NBS" means N-bromosuccinimide.

As used herein, the abbreviation "AIBN" means 2,2'-azobisisobutyronitrile.

As used herein, the abbreviation "DME" means dimethylether.

As used herein, the abbreviation "DIAD" means diisopropylazo-dicarboxylate.

As used herein, the abbreviation "CDI" means 1,1'-carbonyldiimidazole.

As used herein, the abbreviation "MTBE" means methyltertbutylether.

The present invention can be understood more fully by reference to the detailed description and examples, which are intended to exemplify non-limiting embodiments of the invention.

4.2 The Benzopyranone Compounds

As mentioned above, the present invention relates to Benzopyranone Compounds of formula (I):

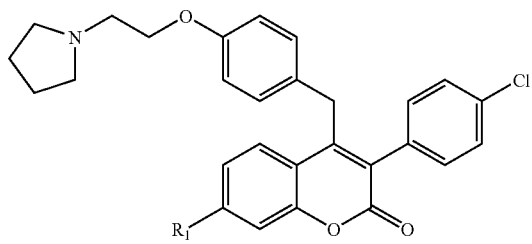

and pharmaceutically acceptable salts thereof, wherein $R_1$ is halogen, trifluoromethyl or $C_1$-$C_6$ alkyl.

In one embodiment, $R_1$ is halogen.

In another embodiment, $R_1$ is trifluoromethyl.

In another embodiment, $R_1$ is $C_1$-$C_6$ alkyl.

In another embodiment, $R_1$ is $C_1$-$C_4$ alkyl.

Illustrative Benzopyranone Compounds are shown below in Table 1:

TABLE 1

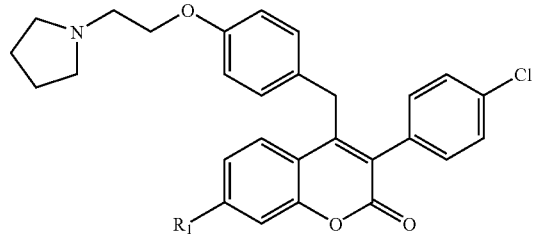

| Compound | $R_1$ |
|---|---|
| A | fluoro |
| B | chloro |
| C | bromo |
| D | iodo |
| E | methyl |
| F | ethyl |
| G | n-propyl |
| H | isopropyl |
| I | sec-butyl |
| J | n-butyl |
| K | isobutyl |
| L | t-butyl |
| M | n-pentyl |
| N | n-hexyl |
| O | trifluoromethyl |

4.3 Methods for Obtaining the Benzopyranone Compounds

The Benzopyranone Compounds can be made by one skilled in the art using known techniques, as well as by the synthetic routes disclosed herein. For example, the Benzopyranone Compounds can be synthesized by the following general Reaction Scheme 1 or Reaction Scheme 2:

Reaction Scheme 1

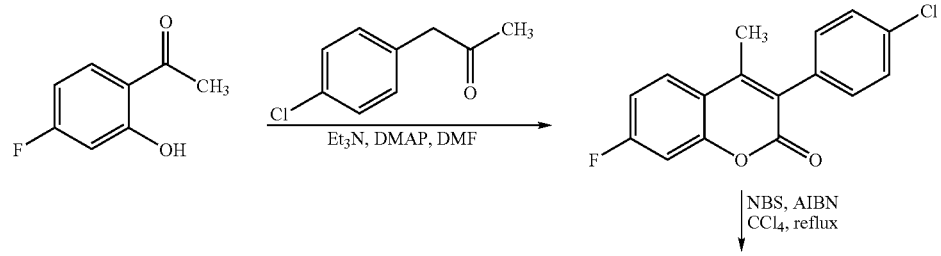

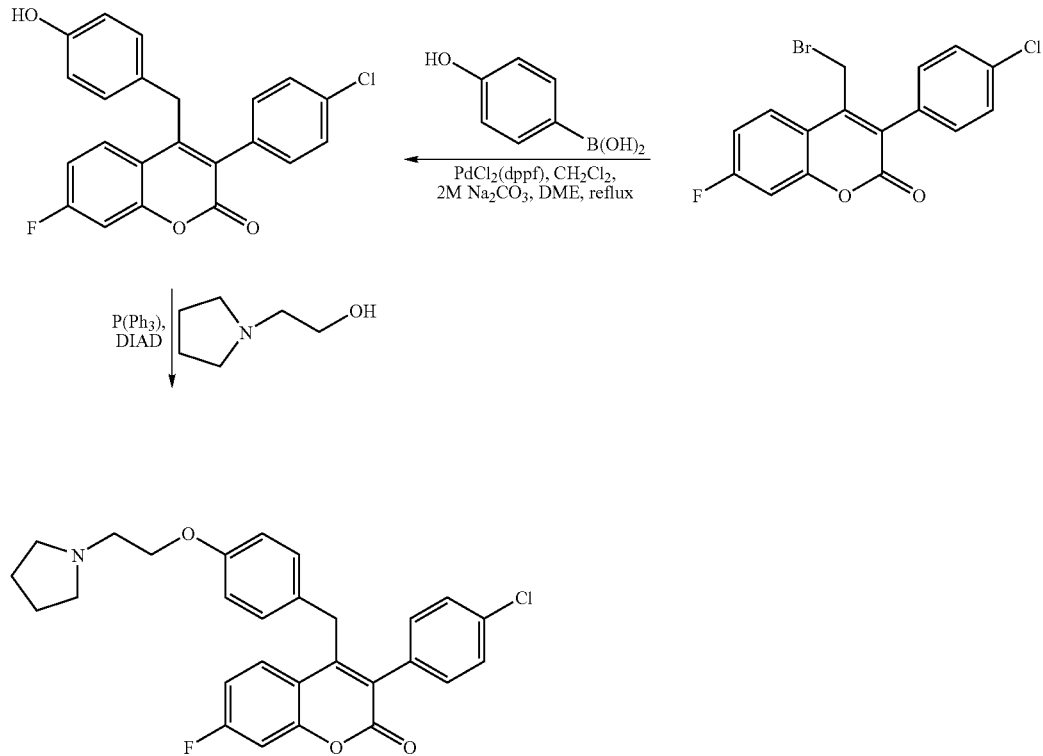
Reaction Scheme 1 yields Benzopyranone Compounds of formula (I) wherein $R_1$ is fluoro.
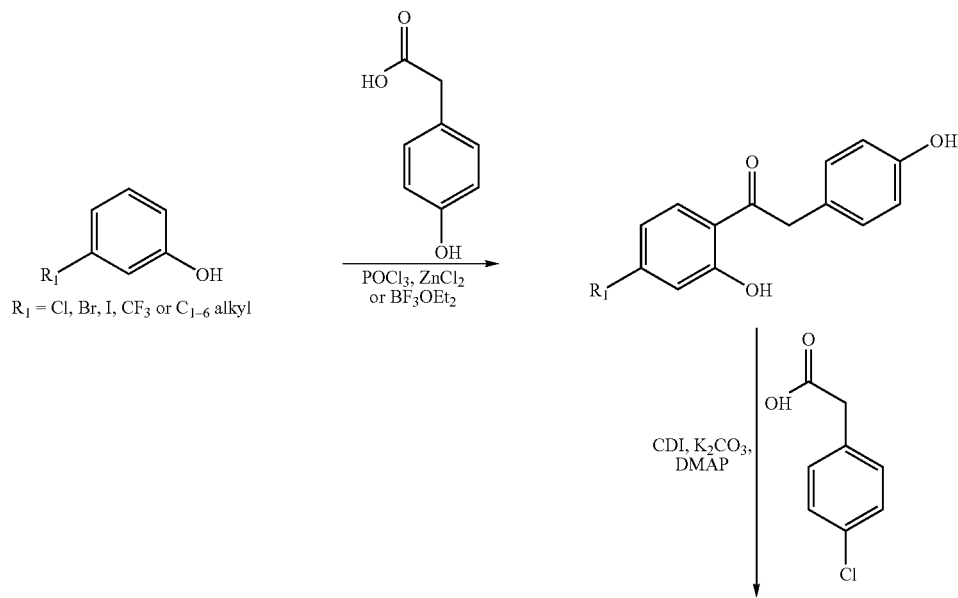

-continued

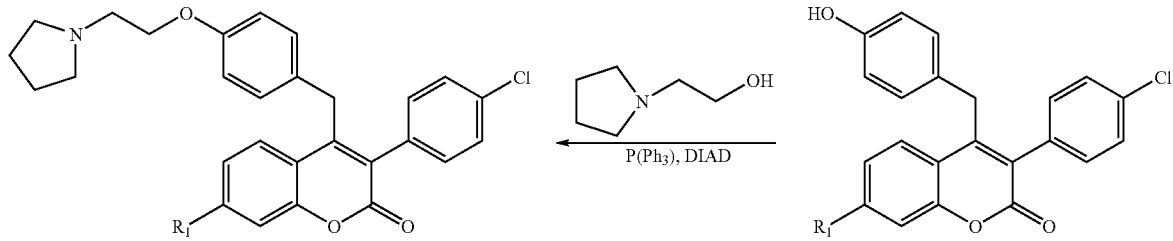

Reaction Scheme 2 depicts methods for obtaining Benzopyranone Compounds of formula (I) wherein $R_1$ is other than fluoro.

Some of the Benzopyranone Compounds can form solvates with water or other organic solvents. Such solvates are similarly included within the scope of this invention.

4.4 Therapeutic and Prophylactic Uses of the Benzopyranone Compounds

Due to their activity, the Benzopyranone Compounds are advantageously useful in veterinary and human medicine. In particular, the Benzopyranone Compounds are useful for the treatment of prevention of cancer.

In one embodiment, the cancer is of the head, neck, eye, mouth, throat, esophagus, chest, bone, lung, colon, rectum, stomach, prostate, breast, ovaries, testicles or other reproductive organs, skin, thyroid, blood, lymph nodes, kidney, liver, pancreas, and brain or central nervous system.

In another embodiment, the cancer has metastasized. In certain embodiments, the metastasized cancer originated in the lung (both small cell or non-small cell), breast, from an unknown primary tumor, a melanoma or colon.

In another embodiment, the cancer is a primary brain cancer.

In certain embodiments, the cancer to be treated or prevented in the present invention includes, but is not limited to, a primary intracranial central nervous system tumor. Primary intracranial central nervous system tumors include glioblastoma multiforme; malignant astrocytomas; oligdendroglioma; ependymoma; low-grade astrocytomas; meningioma; mesenchymal tumors; pituitary tumors; nerve sheath tumors such as schwannomas; central nervous system lymphoma; medulloblastoma; primitive neuroectodermal tumors; neuron and neuron/glial tumors; craniopharyngioma; germ cell tumors; and choroid plexus tumors.

In other embodiments, the cancer to be treated or prevented in the present invention includes, but is not limited to, a primary spinal tumor such as a schwannoma, meningioma, ependymoma, sarcoma, astrocytoma, glioma, vascular tumor, chordoma and epidermoid.

In other embodiments, the cancer to be treated or prevented in the present invention includes, but is not limited to, a primary tumor responsible for brain metastasis such as lung (both small cell and non-small cell), breast, unknown primary, melanoma and colon.

When administered to a patient, e.g., an animal for veterinary use or to a human for clinical use, the Benzopyranone Compounds can be in isolated form. By "isolated" it is meant that prior to administration, a Benzopyranone Compound is separated from other components of a synthetic organic chemical reaction mixture or natural product source, e.g., plant matter, tissue culture, bacterial broth, etc.

In one embodiment, the Benzopyranone Compounds are isolated via conventional techniques, e.g., extraction followed by chromatography, recrystalization, or another conventional technique. When in isolated form, the Benzopyranone Compounds are at least 90%, preferably at least 95%, of a single Benzopyranone Compound by weight of that which is isolated. "Single Benzopyranone Compound" means an enantiomer or a racemate of a Benzopyranone Compound.

The Benzopyranone Compounds are advantageously administered in the form of a composition, in one embodiment a pharmaceutical composition. These compositions can be administered by any convenient route, for example by infusion or bolus injection, by absorption through epithelial or mucocutaneous linings (e.g., oral mucosa, rectal and intestinal mucosa) or via a convection-enhanced drug delivery system and may be administered together with another active agent. Administration can be systemic or local. Various delivery systems are known, e.g., encapsulation in liposomes, microparticles, microcapsules, capsules, and can be used to administer a Benzopyranone Compound of the invention. In certain embodiments, more than one Benzopyranone Compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically to the ears, nose, eyes, or skin. A particular mode of administration can be left to the discretion of the practitioner, and can depend in-part upon the particular site of the cancer.

In one embodiment, the Benzopyranone Compound is administered in combination with another therapeutic agent or prophylactic agent. In a certain embodiment, the therapeutic agent or prophylactic agent is a chemotherapeutic agent.

In another embodiment, it might be desirable to administer one or more Benzopyranone Compounds locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of the primary brain cancer or brain metastasis.

In certain embodiments, it might be desirable to introduce one or more Benzopyranone Compounds into the central nervous system by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the Benzopyranone Compounds can be formulated as a suppository, with traditional binders and carriers such as triglycerides.

In one embodiment, the Benzopyranone Compound is administered via a convection-enhanced drug delivery system. In another embodiment, the Benzopyranone Compound is administered via a convection-enhanced drug delivery system such as that described in U.S. Pat. No. 5,720,720, incorporated by reference herein. Convection-enhanced drug delivery involves positioning the tip of an infusion catheter within a tissue (e.g., brain tissue) and supplying the drug (e.g., a Benzopyranone Compound) through the catheter while maintaining a positive pressure gradient from the tip of the catheter during infusion. The catheter is connected to a pump which delivers the drug and maintains the desired pressure gradient throughout delivery of the drug. Drug delivery rates are typically about 0.5 to about 4.0 ml/min with infusion distances of about 1 cm or more. This method is particularly useful for the delivery of drugs to the brain and other tissue, particularly solid nervous tissue. In certain embodiments, convection-enhanced drug delivery is useful for delivering a Benzopyranone Compound in combination with a high molecular-weight polar molecule such as growth factors, enzymes, antibodies, protein conjugates and genetic vectors to the brain or other tissue. In these embodiments, inflow rates can be up to about 15.0 ml/min.

In another embodiment, the Benzopyranone Compounds of the invention can be delivered in a vesicle, in particular a liposome (see Langer, *Science* 249:1527-1533 (1990); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid.).

In yet another embodiment, the Benzopyranone Compounds can be delivered in a controlled-release system. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, J. Macromol. *Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71: 105 (1989)). In yet another embodiment, a controlled-release system can be placed in proximity of the target of the Benzopyranone Compounds, e.g., the brain, thus requiring only a fraction of the systemic dose (see, e.g., Goodson, in *Medical Applications of Controlled Release*, supra, vol. 2, pp. 115-138 (1984)). Other controlled-release systems discussed in the review by Langer (*Science* 249:1527-1533 (1990)) may be used.

The present compositions comprise an effective amount of a Benzopyranone Compound, in one embodiment in purified form, together with a suitable amount of a pharmaceutically acceptable carrier so as to provide the form for proper administration to the patient.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which a Benzopyranone Compound is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, auxiliary, stabilizing, thickening, lubricating and coloring agents may be used. When administered to a patient, the Benzopyranone Compounds and pharmaceutically acceptable carriers can be sterile. Water is a useful carrier when the Benzopyranone Compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable carrier is a capsule (see e.g., U.S. Pat. No. 5,698,155). Other examples of suitable pharmaceutical carriers are described in "*Remington's Pharmaceutical Sciences*" by E. W. Martin.

In one embodiment, the Benzopyranone Compounds are formulated in accordance with routine procedures as a pharmaceutical composition adapted for intravenous administration to human beings. Typically, Benzopyranone Compounds for intravenous administration are solutions in sterile isotonic aqueous buffer. Where necessary, the compositions can also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the Benzopyranone Compound is to be administered by infusion, it can be dispensed, for example, with an infusion bottle containing sterile pharmaceutical grade water or saline. Where the Benzopyranone Compound is administered by injection, an ampoule of sterile water for injection or saline can be provided so that the ingredients may be mixed prior to administration. Compositions for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered Benzopyranone Compounds. In these later platforms, fluid from the environment surrounding the capsule is imbibed by the driving compound, which swells to displace the agent or agent composition through an aperture. These delivery platforms can provide an essentially zero-order delivery profile as opposed to the spiked profiles of immediate release formulations. A time delay material such as glycerol monostearate or glycerol stearate may also be used. Oral compositions can include standard carriers such as mannitol, lactose, starch, magnesium stearate, sodium saccharine, cellulose or magnesium carbonate. Such carriers can be of pharmaceutical grade.

The amount of the Benzopyranone Compound that is effective for treating or preventing cancer can be determined using standard techniques. In addition, in vitro or in vivo assays may optionally be employed to help identify optimal dosage ranges. An effective dose amount can also depend on the route of administration, and the seriousness of the disease or disorder, and should be decided according to the judgment of the practitioner and each patient's circumstances. However, the general range of effective oral administration amounts of the Benzopyranone Compound is from about 0.5 mg/day to about 5000 mg/day, in one embodiment about 500 mg/day to about 3500 mg/day, in another one embodiment about 1000 mg/day to about 3000 mg/day, in another one embodiment about 1500 mg/day to about 2500 mg/day and in another one embodiment about 2000 mg/day. In another embodiment, effective amounts for intravenous administration are about 10% of an oral dosage amount and effective amounts for convection-enhanced drug administration are about 1% of an oral dosage amount. Of course, it is often practical to administer the daily dose of compound in portions, at various hours of the day. However, in any given case, the amount of Benzopyranone Compound administered will depend on such factors as the solubility of the active component, the formulation used and the route of administration. Suppositories generally contain an effective amount of a Benzopyranone Compound in the range of about 0.5% to about 10% by weight. Oral compositions can contain about 10% to about 95% of Benzopyranone Compound. In some embodiments of the invention, suitable effective dose amounts for oral administration are generally about 10-500 mg of Benzopyranone Compound per kilogram body weight. In other embodiments, the oral effective dose amount is about 10-100, 100-300, 300-900, or 900-1500 mg per kilogram body weight. In other embodiments, the effective oral dose amount is about 100-200, 200-300, 300-400 or 400-500 mg per kilogram body weight. In other embodiments of the invention, effective dose amounts for oral administration are generally 1-7500 micrograms of Benzopyranone Compound per kilogram body weight. In other embodiments, the effective oral dose amount is about 1-10, 10-30, 30-90, or 90-150 micrograms per kilogram body weight. In other embodiments, the effective oral dose amount is about 150-250, 250-325, 325-450, 450-1000 or 1000-7500 micrograms per kilogram body weight. Effective dose amounts can be extrapolated from dose-response curves derived from in vitro or animal model test systems. Such animal models and systems are well known in the art.

The invention also provides pharmaceutical packs or kits comprising one or more containers containing one or more Benzopyranone Compounds. Optionally associated with such container(s) can be a notice in the form prescribed by a governmental agency regulating the manufacture, use or sale of pharmaceuticals or biological products, which notice reflects approval by the agency of manufacture, use or sale for human administration. In certain embodiments, the kit may also contain one or more other chemotherapeutic agents that can be administered prior to, subsequent to or concurrently with a Benzopyranone Compound.

The Benzopyranone Compounds can be assayed in vitro, and then in vivo, for the desired therapeutic or prophylactic activity, prior to use in humans. For example, in vitro assays can be used to determine whether administration of a specific Benzopyranone Compound or combination of Benzopyranone Compounds is preferred.

In one embodiment, a patient tissue sample is grown in culture, and contacted or otherwise administered with a Benzopyranone Compound, and the effect of the Benzopyranone Compound upon the tissue sample is observed and compared with a non-contacted tissue. In other embodiments, a cell culture model is used in which the cells of the cell culture are contacted or otherwise administered with a Benzopyranone Compound, and the effect of such Benzopyranone Compound upon the tissue sample is observed and compared with a non-contacted cell culture. Generally, a lower level of proliferation or survival of the contacted cells compared to the non-contracted cells indicates that the Benzopyranone Compound is effective to treat a patient having cancer. Such Benzopyranone Compounds may also be demonstrated effective and safe using animal model systems.

The Benzopyranone Compounds can be in the form of a pharmaceutically acceptable salt. Pharmaceutically acceptable are conveniently formed, as is usual in organic chemistry, by reacting a free-base form of a Benzopyranone Compound with a suitable acid, such as have been described above. The salts can be formed in high yields at moderate temperatures, and can be prepared by isolating the salt form of a Benzopyranone Compound from a suitable acidic wash in the final step of a synthesis. The salt-forming acid can be dissolved in an anhydrous or a water-containing organic solvent, such as an alkanol, such as methanol, ethanol or isopropanol; ketone, such as acetone; or ester, such as ethyl acetate. On the other hand, if a free-base form of a Benzopyranone Compound is desired, it can be isolated from a basic final wash step. A typical technique for preparing hydrochloride salts is to dissolve the free base in a suitable solvent and dry the solution thoroughly, as over molecular sieves, before bubbling hydrogen chloride gas through it.

4.5 Additional Therapies

The methods for treating or preventing cancer comprising the administration of an effective amount of a Benzopyranone Compound can further comprise the administration of an effective amount of other therapy. The other therapy includes, but is not limited to, chemotherapy, radiation therapy, hormonal therapy, a bone marrow transplant, stem-cell replacement therapy, another biological therapy and an immunotherapy.

In one embodiment, the methods of the invention further comprise the administration of an angiogenesis inhibitor such as but not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta;

Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; an antiinflammatory steroid such as but not limited to dexamethasone; a Metalloproteinase inhibitor (TIMP); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; a Retinoids Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; a farnesyl transferase inhibitor (FTI); and a bisphosphonate (e.g., alendronate, etidronate, pamidronate, risedronate, ibandronate, zoledronate, olpadronate, icandronate or neridronate).

The other therapy can be the administration of an anti-cancer agent. Useful anti-cancer agents include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; erbitux; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; ImiDs™; interleukin II (including recombinant interleukin II, or rIL2), interferon-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; SelCid™; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. In one embodiment the anti-cancer agent is 5-fluorouracil or leucovorin, which can also be administered prior to, subsequent to or concurrently with the administration of an effective amount of thalidomide or a topoisomerase inhibitor.

The other therapy can be radiation therapy, comprising the use of x-rays, gamma rays and other sources of radiation to destroy the cancer cells. In some embodiments, the radiation treatment is administered as external beam radiation or teletherapy wherein the radiation is directed from a remote source. In other embodiments, the radiation treatment is administered as internal therapy or brachytherapy wherein a radioactive source is placed inside the body close to cancer cells or a tumor mass.

4.6 Inhibition of Cancer and Neoplastic Cells and Disease

The Benzopyranone Compounds can be demonstrated to inhibit tumor cell proliferation, cell transformation and/or tumorigenesis in vitro and in vivo using a variety of assays known in the art, or described herein. Such activity can be demonstrated in an in vitro assay by contacting a Benzopyranone Compound of the present invention with a tumor cell. In general, a tumor cell is exposed to varying concentrations of a Benzopyranone Compound, followed by measuring cell survival relative to a control. Such assays may use cells of a cancer cell line, or cells from a patient. Many assays well-known in the art can be used to assess such survival and/or growth; for example, cell proliferation can be assayed by measuring ($^3$H)-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as Western blotting or immunoprecipitation using commercially available antibodies (for example, many cell-cycle marker antibodies are from Santa Cruz Inc.). mRNA can be quantitated by methods that are well known and routine in the art, for example, using northern analysis, RNase protection or the polymerase chain reaction in connection with the reverse transcription. Cell viability can be assessed by using trypan-blue staining or other cell death or viability markers known in the art. Differentiation can be assessed visually based on changes in morphology, for example.

The Benzopyranone Compounds can also be demonstrated to inhibit glioma tumor cell proliferation, cell transformation and tumorigenesis in vitro and in vivo using a variety of assays known in the art, or described herein. Such activity can be demonstrated in an in vitro assay by contacting a Benzopyranone Compound with a glioma tumor cell. (Haroun, R. I. et al., *J. Neurooncol.* 58:115-23 (2002); Sharma A. et al., *J. Mol. Neurosci.* 17:331-9 (2001); Iwadate Y. et al., *Int. J. Mol. Med.* 10:187-92 (2002)).

The present invention provides for cell-cycle and cell-proliferation analysis by a variety of techniques known in the art, including but not limited to the following examples.

As one example, bromodeoxyuridine (BRDU) incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino et al., *Int. J. Cancer* 38:369 (1986); Campana et al., *J. Immunol. Meth.* 107:79 (1988)).

Cell proliferation may also be examined using ($^3$H)-thymidine incorporation (see e.g., Chen, J., *Oncogene* 13:1395-403 (1996); Jeoung, J., *J. Biol. Chem.* 270:18367-73 (1995)). This assay allows for quantitative characterization of S-phase DNA synthesis. In this assay, cells synthesizing DNA will incorporate ($^3$H)-thymidine into newly synthesized DNA. Incorporation may then be measured by standard techniques in the art such as by counting of radioisotope in a Scintillation counter (e.g. Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., *Curr. Biol.* 6:189-199 (1996); Vassilev et al., *J. Cell Sci.* 108:1205-15 (1995)).

Cell proliferation may be measured by counting samples of a cell population over time (e.g. daily cell counts). Cells may be counted using a hemacytometer and light microscopy (e.g. HyLite hemacytometer, Hausser Scientific). Cell number may be plotted against time in order to obtain a growth curve for the population of interest. In a preferred embodiment, cells counted by this method are first mixed with the dye Trypan-blue (Sigma), such that living cells exclude the dye, and are counted as viable members of the population.

DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g. cells in S-phase) will exhibit a ploidy value higher than 2N and up to 4N DNA content. Ploidy value and cell-cycle kinetics may be further measured using propidum iodide assay (see e.g. Turner, T., et al., *Prostate* 34:175-81 (1998)). Alternatively, the DNA ploidy may be determined by quantitation of DNA Feulgen staining (which binds to DNA in a stoichiometric manner) on a computerized microdensitometrystaining system (see e.g., Bacus, S., *Am. J. Pathol.* 135:783-92 (1989)). In an another embodiment, DNA content may be analyzed by preparation of a chromosomal spread (Zabalou, S., *Hereditas* 120:127-40 (1994); Pardue, *Meth. Cell Biol.* 44:333-351 (1994)).

The expression of cell-cycle proteins (e.g., CycA. CycB, CycE, CycD, cdc2, Cdk4/6, Rb, p21, p27, etc.) provide crucial information relating to the proliferative state of a cell or population of cells. For example, identification in an anti-proliferation signaling pathway may be indicated by the induction of p21$^{cip1}$. Increased levels of p21 expression in cells results in delayed entry into G1 of the cell cycle (Harper et al., *Cell* 75:805-816 (1993); Li et al., *Curr. Biol.* 6:189-199 (1996)). p21 induction may be identified by immunostaining using a specific anti-p21 antibody available commercially (e.g. Santa Cruz). Similarly, cell-cycle proteins may be examined by Western blot analysis using commercially available antibodies. In another embodiment, cell populations are synchronized prior to detection of a cell cycle protein. Cell cycle proteins may also be detected by FACS (fluorescence-activated cell sorter) analysis using antibodies against the protein of interest.

Detection of changes in length of the cell-cycle or speed of cell-cycle may also be used to measure inhibition of cell proliferation by the Benzopyranone Compounds. In one embodiment the length of the cell-cycle is determined by the doubling time of a population of cells (e.g., using cells contacted or not contacted with one or more Benzopyranone Compounds of the invention). In another embodiment, FACS analysis is used to analyze the phase of cell-cycle progression, or purify G1, S, and G2/M fractions (see e.g., Delia, D. et al., *Oncogene* 14:2137-47 (1997)).

Lapse of cell-cycle checkpoint(s), and/or induction of cell-cycle checkpoint(s), may be examined by the methods described herein, or by any method known in the art. Without limitation, a cell-cycle checkpoint is a mechanism which ensures that a certain cellular events occur in a particular order. Checkpoint genes are defined by mutations that allow late events to occur without prior completion of an early event (Weinert, T., and Hartwell, L., *Genetics*, 134:63-80 (1993)). Induction or inhibition of cell-cycle checkpoint genes may be assayed, for example, by Western blot analysis, or by immunostaining, etc. Lapse of cell-cycle checkpoints may be further assessed by the progression of a cell through the checkpoint without prior occurrence of specific events (e.g., progression into mitosis without complete replication of the genomic DNA).

In addition to the effects of expression of a particular cell-cycle protein, activity and post-translational modifications of proteins involved in the cell-cycle can play an integral role in the regulation and proliferative state of a cell. The invention provides for assays involved detected post-translational modifications (e.g. phosphorylation) by any method known in the art. For example, antibodies that detect phosphorylated tyrosine residues are commercially available, and may be used in Western blot analysis to detect proteins with such modifications. In another example, modifications such as myristylation, may be detected on thin layer chromatography or reverse phase h.p.l.c. (see e.g., Glover, C., *Biochem. J.* 250:485-91 (1988); Paige, L., *Biochem J.* 250:485-91 (1988)).

Activity of signaling and cell cycle proteins and/or protein complexes is often mediated by a kinase activity. The present invention provides for analysis of kinase activity by assays such as the histone H1 assay (see e.g., Delia, D. et al., *Oncogene* 14:2137-47 (1997)).

The Benzopyranone Compounds can also be demonstrated to alter cell-proliferation in cultured cells in vitro using methods which are well known in the art. Specific examples of cell-culture models for primary brain cancer and brain metastasis include, but are not limited to, those found in the following U.S. Pat. Nos. 6,194,158; 6,051,376 and 6,071,696.

The Benzopyranone Compounds can also be demonstrated to inhibit cell transformation (or progression to malignant phenotype) in vitro. In this embodiment, cells with a transformed cell phenotype are contacted with one or more Benzopyranone Compounds, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, *General Virology*, 3d Ed., John Wiley & Sons, New York, pp. 436-446).

Loss of invasiveness or decreased adhesion may also be used to demonstrate the anti-cancer effects of the Benzopyranone Compounds. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell-cell adhesion. Such E-cadherin-mediated adhesion can result in phenotypic reversion and loss of invasiveness (Hordijk et al., *Science* 278:1464-66 (1997)).

Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF-induced cell scattering is correlated with invasiveness of cells such as Madin-Darby canine kidney (MDCK) cells. This assay identifies a cell population that has lost cell scattering activity in response to HGF (Hordijk et al., *Science* 278:1464-66 (1997)).

Alternatively, loss of invasiveness may be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see e.g., Ohnishi, T., *Biochem. Biophys. Res. Commun.* 193:518-25 (1993)).

The Benzopyranone Compounds can also be demonstrated to inhibit tumor formation in vivo. A vast number of animal models of hyperproliferative disorders, including tumorigenesis and metastatic spread, are known in the art (see Table 317-1, Chapter 317, "Principals of Neoplasia," in *Harrison's Principals of Internal Medicine*, 13th Edition, Isselbacher et al., eds., McGraw-Hill, New York, p. 1814, and Lovejoy et al., 1997, *J. Pathol.* 181:130-135). Specific examples for primary brain cancer and brain metastasis can be found in the following U.S. Pat. Nos. 5,894,018; 6,028, 174 and 6,203,787, which are incorporated by reference herein. Further, general animal models applicable to many types of cancer have been described, including, but not restricted to, the p53-deficient mouse model (Donehower, 1996, *Semin. Cancer Biol.* 7:269-278), the Min mouse (Shoemaker et al., *Biochem. Biophys. Acta*, 1332:F25-F48 (1997)), and immune responses to tumors in rat (Frey, *Methods*, 12:173-188 (1997)).

For example, a Benzopyranone Compound can be administered to a test animal, preferably a test animal predisposed to develop a tumor, and the test animal subsequently examined for an decreased incidence of tumor formation in comparison with controls not administered the Benzopyranone Compound. Alternatively, a Benzopyranone Compound can be administered to test animals having a tumor (e.g., animals in which a tumor has been induced by introduction of malignant, neoplastic, or transformed cells, or by administration of a carcinogen) and subsequently examining the tumor in the test animals for tumor regression in comparison to control animals not administered the Benzopyranone Compound.

The following illustrative examples are set forth to assist in understanding the invention and do not limit the invention described and claimed herein.

The following examples are non-limiting aspects of the invention.

5. EXAMPLES

Examples 1 and 2 relate to the synthesis of illustrative Benzopyranone Compounds.

Example 1

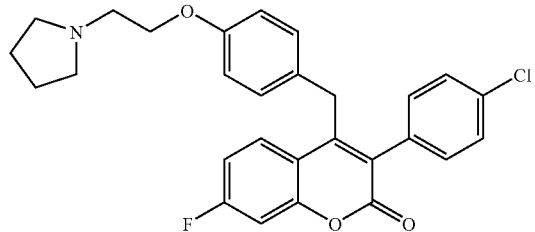

3-(4-Chloro-phenyl)-7-fluoro-4-[4-(2-pyrrolidin-1-yl-ethoxy)-benzyl]-chromen-2-one A solution of 4-chlorophenylacetic acid (11.05 g, 64.8 mmol) in DMF (100 mL) was treated with CDI (13.13 g, 81 mmol) in several portions over about 15 minutes and the mixture was stirred until gas evolution had ceased. 4-Fluoro-2-hydroxyacetophenone (5.0 g, 32.4 mmol) was added followed by potassium carbonate (15.7 g, 113.6 mmol) and 4-DMAP (about 1 g). The reaction mixture was warmed at about 80° C. for about 10 h then cooled to room temperature. Water (200 mL) was added and the aqueous layer was extracted with ethyl acetate. The combined organic layer was concentrated and the crude product was purified by flash chromatography (ethyl acetate/hexanes) to give a yield of about 3.5 g (38%) of a benzopyranone intermediate.

A solution of the benzopyranone intermediate (1.85 g, 6.8 mmol) in $CCl_4$ (20 mL) was treated with NBS (1.33 g, 7.5 mmol) and AIBN (0.09 g, 0.5 mmol) and the mixture was heated at reflux for about 15 hours. The reaction mixture was concentrated, providing a crude product that was purified using flash chromatography (ethyl acetate/hexanes) to provide about 2.6 g (92%) of a bromomethyl-benzopyranone.

A solution of the bromomethyl-benzopyranone (1.0 g, 2.72 mmol) and 4-hydroxyphenylboronic acid (0.56 g, 4.1 mmol) in THF (30 mL) was treated with 2 M sodium carbonate (5 mL) and (1,1'-bis(diphenylphosphino)ferrocene)-dichloropalladium (II) dichloromethane complex (0.1 g, 0.14 mmol). The reaction mixture was heated at reflux for about 6 hours then cooled to room temperature. The crude product was purified using flash chromatography (ethyl acetate/hexanes) to provide about 0.30 g (30%) of a phenolbenzopyranone.

A solution of the phenolbenzopyranone (0.28 g, 0.74 mmol), triphenylphosphine (0.28 g, 1.1 mmol), and 1-(2-hydroxyethyl)pyrrolidine (0.13 g, 1.1 mmol) in THF/CH$_2$Cl$_2$ (1:1, 8 mL) was treated with DIAD (0.22 g, 1.1 mmol) and the reaction mixture was stirred at room temperature for about 6 hours. The reaction mixture was concentrated and the crude product was purified using flash chromatography (methylene chloride/methanol) to provide about 35 mg (10%) of 13-(4-Chlorophenyl)-7-fluoro-4-[4-(2-piperidin-1-yl-ethoxy)-benzyl-]-chromen-2-one.

Example 2

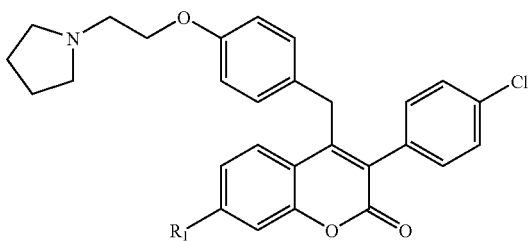

7-substituted 3-(4-chlorophenyl)-4-[4-(2-pyrrolidin-1-yl-ethoxy)-benzyl]-chromen-2-one analogs Under a N$_2$ atmosphere a phenol substituted at its 3-position with R$_1$, defined above, and 4-hydroxyphenylacetic acid (1.2 equivalents) are suspended in chlorobenzene. Boron trifluoride diethyl etherate (3 equivalents) is added at about 20 to about 25° C. in about 5 minutes. The suspension is heated to about 80° C. and stirred for about 4-5 hours then left to cool overnight.

The precipitated solid is filtered with N$_2$-pressure and the filtrate is directly quenched by pouring it onto cold water (about 0 to about 5° C.) (slightly exothermic). The resulting filter cake is washed with CH$_2$Cl$_2$. Saturated aqueous sodium carbonate is added to the filtrate within about 10 to about 15 minutes and foaming is observed. The resulting solid is stirred at about 20° C. overnight. The suspension is filtered, washed with H$_2$O and MTBE (3×) and dried under N$_2$-pressure overnight. The resulting product is dried in vacuo at about 40° C. to achieve constant weight.

4-Chlorophenylacetic acid (2 equivalents) is dissolved in DMF and stirred at about 18° C. CDI (2 equivalents) is added slowly within about 15 minutes to the clear green/yellow solution. During the CDI addition gas evolution (CO$_2$) is observed. The mixture is heated to about 55° C., stirred for about 25 minutes at this temperature and cooled down to about 10° C. K$_2$CO$_3$ (2 equivalents), DMAP (0.2 equivalents), and the product of the immediately preceding paragraph is added to the yellow/brown suspension and the suspension is warmed to about 94 to about 96° C. and stirred for about 1 hour.

The K$_2$CO$_3$ is filtered and washed with DMF. The filtrate is poured into cold H$_2$O while vigorously stirring and the mixture is stirred for another about 1 to 2 hours. The suspension is cooled to about 0 to about 5° C. and the solid is filtered. The filter cake is distributed between MTBE and 1.5 M HCl. The water layer is extracted with MTBE. The combined organic layers are washed with saturated aqueous NaHCO$_3$. The organic phase is concentrated to approximately 1.5 to 1.7 M solution (0.6 to 0.65 L/mol) and diluted with EtOAc. The resulting suspension is heated to about 55° C. and stirred for about 15 minutes and cooled to about 0° C. over about 3 to about 4 hours. The resulting product is filtered and washed with cold MTBE/EtOAc 5:1 (about −20 to about −25° C.) and dried under a flow of N$_2$ overnight.

A solution of the product of the immediately preceding paragraph (1 equivalent), triphenylphosphine (2 equivalents), and 1-(2-hydroxyethyl)pyrrolidine (3 equivalents) in THF/CH$_2$Cl$_2$ is treated with DIAD (1.8 equivalents) and the reaction mixture is stirred at room temperature for about 6 hours. The solvent is removed and the crude product is purified by flash chromatography to provide a 7-substituted 3-(4-chlorophenyl)-4-[4-(2-piperidin-1-yl-ethoxy)-benzyl]-chromen-2-one compound.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited, the entire disclosures of which are incorporated herein by reference.

What is claimed is:

1. A method for treating cancer in a patient wherein the cancer is selected from the group consisting of the head, neck, eye, mouth, throat, esophagus, chest, bone, lung, colon, rectum, stomach, prostate, breast, ovary, testicle or other reproductive organ, skin, thyroid, blood, lymph node, kidney, liver, pancreas or brain, comprising
   administering to a patient in need thereof an effective amount of a compound of the formula:

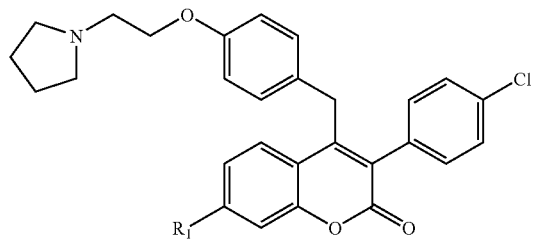

or a pharmaceutically acceptable salt thereof, wherein R$_1$ is halogen, trifluoromethyl or C$_{1-6}$ alkyl.

2. The method of claim 1 wherein R$_1$ is halogen.
3. The method of claim 2 wherein halogen is fluoro.
4. The method of claim 1 wherein R$_1$ is C$_{1-6}$ alkyl.
5. The method of claim 4 wherein C$_{1-6}$ alkyl is methyl.
6. The method of claim 4 wherein C$_{1-6}$ alkyl is ethyl.
7. The method of claim 4 wherein C$_{1-6}$ alkyl is n-propyl.
8. The method of claim 4 wherein C$_{1-6}$ alkyl is isopropyl.
9. The method of claim 4 wherein C$_{1-6}$ alkyl is t-butyl.
10. The method of claim 1 wherein R$_1$ is trifluoromethyl.
11. The method of claim 1 wherein the cancer is a primary brain cancer.

* * * * *